US011834431B2

(12) United States Patent
Takahashi et al.

(10) Patent No.: US 11,834,431 B2
(45) Date of Patent: Dec. 5, 2023

(54) CRYSTALS OF CYCLIC AMINE DERIVATIVE AND PHARMACEUTICAL USE THEREOF

(71) Applicant: Toray Industries, Inc., Tokyo (JP)

(72) Inventors: Hirozumi Takahashi, Kanagawa (JP); Yoko Baba, Kanagawa (JP); Yasuhiro Morita, Kanagawa (JP); Katsuhiko Iseki, Shiga (JP); Naoki Izumimoto, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 528 days.

(21) Appl. No.: 17/172,240

(22) Filed: Feb. 10, 2021

(65) Prior Publication Data

US 2021/0198236 A1 Jul. 1, 2021

Related U.S. Application Data

(62) Division of application No. 16/326,580, filed as application No. PCT/JP2017/030528 on Aug. 25, 2017, now Pat. No. 10,961,217.

(30) Foreign Application Priority Data

Aug. 26, 2016 (JP) .................... 2016-165437

(51) Int. Cl.
C07D 401/06 (2006.01)

(52) U.S. Cl.
CPC ........ C07D 401/06 (2013.01); *C07B 2200/13* (2013.01)

(58) Field of Classification Search
CPC .................................................. C07D 401/06
See application file for complete search history.

(56) References Cited

U.S. PATENT DOCUMENTS

| 6,627,646 | B2 | 9/2003 | Bakale et al. |
| 10,173,999 | B2 | 1/2019 | Arai et al. |
| 2016/0194302 | A1 | 7/2016 | Morita et al. |
| 2018/0065950 | A1 | 3/2018 | Arai et al. |

FOREIGN PATENT DOCUMENTS

| CN | 107250128 A | 10/2017 |
| FR | 2 567 885 A1 | 1/1986 |
| GB | 2 163 150 A | 2/1986 |
| JP | 61-37765 A | 2/1986 |
| JP | 2006-8664 A | 1/2006 |
| JP | 2017-57200 A | 3/2017 |
| WO | 03/031432 A1 | 4/2003 |
| WO | 2013/147160 A1 | 10/2013 |
| WO | 2015/046403 A1 | 4/2015 |
| WO | 2016/136944 A1 | 9/2016 |

OTHER PUBLICATIONS

A. Okifuji et al., "Management of Fibromyalgia Syndrome: Review of Evidence," Pain and Therapy, 2013, vol. 2, pp. 87-104.
The First Chinese Office Action dated Jul. 16, 2020 of counterpart Chinese Application No. 201780051578.1 with an English translation.
Mexican Office Action dated Jul. 29, 2020 of counterpart Mexican Application No. MX/a/2019/001380.
Bernstein, "Polymorphism in . . . ," pp. 115-118, 272. (Year: 2002).
Davidovich et al., "Detection of polymorphism . . . ," Am. Pharm. Rev. 7(1), pp. 10, 12, 14, 16, 100 . . . (Year: 2004).
Dean, "Analytical Chem . . . ," pp. 10.24-10.26 (Year: 1995).
Ivanisevic et al., "Use of X-ray . . . ," Pharm. Sci. Encycl., pp. 1-42 (Year: 2010).
Seddon, "Pseudopolymorph . . . ," Crystal Growth & Design, vol. 4(6), p. 1087 (2 pages from Internet) (Year: 2004).
Rodriguez-Spong et al., "General principles, etc.," Adv. Drug Delivery Reviews, 56, pp. 241-274 (Year: 2004).
Kirk-Othmer, Encyclopedia of Chemical Technology, 8, pp. 95-147 (Year: 2002).
Vippagunta et al., "Crystalline Solids," Advanced Drug Delivery Reviews, 48, pp. 3-26 (Year 2001).
Guillory (in Brittain ed.), "Polymorphism in Pharmaceutical Solids," NY: Marcel Dekker, Inc., 1-2, pp. 183-226 *(Year: 1999).
Braga et al., "Making crystals from . . . ," J. Royal Soc. Chem. Commun., pp. 3635-3645 (Year: 2005).
CMU Pharmaceutical polymorphism, Internet, pp. 1-3 printout Apr. 3, 2008 (Year: 2002).
Singhal et al., "Drug Polymorphism, etc.," Advanced Drug Delivery reviews, 56, pp. 335-347 (Year: 2004).
Concise Encyclopedia Chemistry, NY: Walter de Gruyter, pp. 872-873 (Year: 1993).
Jain et al., "Polymorphism in Pharmacy," Indian Drugs, vol. 23(6), pp. 315-329 (Year: 1986).
Muzaffar et al., "Polymorphism and Drug Availability, etc.," J of Pharm. (Lahore), vol. 1(1), pp. 59-66 (Year: 1979).
US Pharmacopia #23, National Formulary #18, pp. 1843-1844 (Year: 1995).
Doelker, English translation of S.T.P., Pratiques, vol. 9(5), 399-409 , pp. 1-33 (Year: 1999).
Doelker, English translation of Ann. Pharm. Fr., 60:161-176, pp. 1-39 (Year: 2002).
Taday et al., "Using Terahertz, etc.," J of Pharm. Sci., vol. 92(4), pp. 831-838 (Year: 2003).
Otuska et al., "Effect of Polymorphis, etc.," Chem. Pharm. Bull., vol. 47(6), 852-8569 (Year: 1999).
Substantive Examination Report dated Jun. 16, 2023, of counterpart Filipino Patent Application No. 1/2019/500287.

*Primary Examiner* — Rebecca L Anderson
(74) *Attorney, Agent, or Firm* — DLA Piper LLP (US)

(57) ABSTRACT

A crystal of ethane disulfonate of (S)-1-(4-(dimethylamino) piperidin-1-yl)-3-hydroxy-3-(1-methyl-1H-imidazol-2-yl) propan-1-one, having peaks at diffraction angles 2θ)(° of 12.6±0.2, 16.0±0.2, 17.7±0.2, 18.5±0.2, and 21.3±0.2 in powder X-ray diffraction; and the crystal of ethane disulfonate of (S)-1-(4-(dimethylamino)piperi din-1-yl)-3-hydroxy-3-(1-methyl-1H-imidazol-2-yl)propan-1-one, having an endothermic peak at 173° C. to 177° C. in simultaneous thermogravimetric-differential thermal analysis.

2 Claims, 6 Drawing Sheets

CRYSTALS OF CYCLIC AMINE DERIVATIVE AND PHARMACEUTICAL USE THEREOF

TECHNICAL FIELD

This disclosure relates to a crystal of a cyclic amine derivative and a pharmaceutical use thereof.

BACKGROUND

Pain refers to an unpleasant sensory and emotional experience with actual or potential tissue damage. Pain is mainly classified as nociceptive pain, neuropathic pain, or psychogenic pain due to its cause. In addition, fibromyalgia syndrome is known as a pain with an unknown cause.

Neuropathic pain is a pathological pain due to a dysfunction of the peripheral or central nervous system itself, which refers to a pain caused by direct damage or oppression of the nerve tissue despite the fact that the nociceptor is not subjected to a noxious stimulation. Anticonvulsants, antidepressants, anxiolytics, and antiepileptics such as gabapentin and pregabalin are used as therapeutic agents for neuropathic pain.

Fibromyalgia syndrome is a disease accompanied by systemic pain as the main symptom and secondary symptoms including neuropsychiatric and neurovegetative symptoms. As therapeutic agents for fibromyalgia syndrome, pregabalin approved in the United States and Japan and duloxetine and milnacipran approved in the United States are mainly used. Nonsteroidal anti-inflammatory agents, opioid compounds, antidepressants, anticonvulsants, and antiepileptics, that are not approved as therapeutic agents for fibromyalgia syndrome, are also used. Therapeutic effects of nonsteroidal anti-inflammatory agents and opioid compounds are usually considered to be weak (Okifuji et al., Pain and Therapy, 2013, vol. 2, pp. 87-104).

French Patent No. 2567885 discloses that certain types of substituted piperidines have cardiotonic activity. JP Patent Publication (Kokai) No. 2006-008664 discloses that imidazole derivatives show the FXa inhibitory action. International Publication WO 2003/031432 suggests that substituted piperidines have a potential drug efficacy against overweight or obesity. International Publication WO 2013/147160 and International Publication WO 2015/046403 disclose that imidazole derivatives have the analgesic action.

In addition, pharmaceutical products need to maintain quality over long-term processes of distribution, storage and the like, and chemical compounds to be contained as active ingredients are required to have high levels of chemical and physical stability. Therefore, in general, for an active ingredient of a pharmaceutical product, the crystal which is expected to have higher stability than an amorphous matter is employed. If such a crystal is obtained, the purification effect by recrystallization upon production can be expected. Further, the crystal which has low hygroscopicity from the viewpoints of maintaining stability and handling during production, storage, formulation, and analysis of a drug substance is preferable.

To obtain a crystal of a compound to be an active ingredient of a pharmaceutical product, it is necessary to examine various conditions for precipitating crystals from a solution. It is common to select a solvent in which the solubility of the compound at room temperature is not so large and to perform crystallization under conditions in which the compound is dissolved to result in a possible highest concentration.

However, in the treatment with conventional therapeutic agents for neuropathic pain, it is highly frequent that side effects of the central nervous system such as dizziness, nausea or vomiting occur. To enable long-term administration, the development of a novel therapeutic agent for neuropathic pain has been awaited.

Even pregabalin, duloxetine and milnacipran, that are approved as therapeutic agents for fibromyalgia syndrome, do not have clinically satisfying therapeutic effects on fibromyalgia syndrome. In addition, as the difference in efficacy among patients is also large, the development of a novel therapeutic agent for fibromyalgia syndrome which has strong pharmacological activity and exerts therapeutic effects on a wide variety of patients has been desired.

Further, in consideration of one dose package with other agents, it is preferable that novel therapeutic agents for neuropathic pain and therapeutic agents for fibromyalgia syndrome that can solve the above problems are crystals that have low hygroscopicity and excellent solubility and chemical and physical stability, and it is more preferable that such crystals can be expected to have the purification effect upon production.

French Patent No. 2567885 suggests that the described substituted piperidines are effective for migraine, and International Publication WO 2013/147160 and International Publication WO 2015/046403 disclose that the described imidazole derivatives have the analgesic action. However, French Patent No. 2567885, International Publication WO 2013/147160 and International Publication WO 2015/046403 fail to disclose the compound herein revealed to have the analgesic action or suggest the relationship between the analgesic action and the chemical structure thereof. Regarding the imidazole derivative described in JP Patent Publication (Kokai) No. 2006-008664 and the substituted piperidines described in International Publication WO 2003/031432, it is neither disclosed nor suggested that they have at least a possibility of having the analgesic action.

Furthermore, French Patent No. 2567885, JP Patent Publication (Kokai) No. 2006-008664, International Publication WO 2003/031432, International Publication WO 2013/147160 and International Publication WO 2015/046403 fail to teach crystallization of the disclosed compounds, and also fail to suggest a possibility of acquiring promising crystals as pharmaceutical products.

Accordingly, it could be helpful to provide a crystal that is useful as a pharmaceutical product of a compound having the analgesic action on neuropathic pain and/or fibromyalgia syndrome.

SUMMARY

We found a compound having a strong analgesic action against pain and, in particular, neuropathic pain and/or fibromyalgia syndrome, and further found a crystal of the compound having low hygroscopicity and excellent solubility and chemical and physical stability.

Specifically, we provide a crystal of (S)-1-(4-(dimethylamino)piperidin-1-yl)-3-hydroxy-3-(1-methyl-1H-imidazol-2-yl)propan-1-one (hereinafter referred to as "compound (I)") represented by chemical formula (I) or of a pharmacologically acceptable salt thereof.

(I)

The above crystal is preferably a crystal having peaks at diffraction angles 2θ)(° of 15.3, 16.0, 19.0, 21.8, and 23.0 in powder X-ray diffraction, and it is more preferably a crystal having an endothermic peak at 120° C. to 124° C. in simultaneous thermogravimetric—differential thermal analysis.

The above crystal is a crystal having low hygroscopicity and excellent solubility and chemical and physical stability as a pharmaceutical product, and has the purification effect upon production.

The above pharmacologically acceptable salt is preferably ethane disulfonate. A crystal of ethane disulfonate of compound (I) is preferably a crystal having peaks at diffraction angles 2θ)(° of 12.6, 16.0, 17.7, 18.5, and 21.3 in powder X-ray diffraction, and it is more preferably a crystal having an endothermic peak at 173° C. to 177° C. in simultaneous thermogravimetric—differential thermal analysis.

The above crystal is a crystal having low hygroscopicity and excellent solubility and chemical and physical stability as a pharmaceutical product, and has the purification effect upon production.

In addition, we provide a medicine comprising the crystal of compound (I) or of the pharmacologically acceptable salt thereof as an active ingredient.

The medicine is preferably an analgesic agent and more preferably a therapeutic agent for neuropathic pain or fibromyalgia syndrome.

The therapeutic agent for neuropathic pain or the therapeutic agent for fibromyalgia syndrome exerts an excellent analgesic action and, in particular, a therapeutic effect on neuropathic pain or fibromyalgia syndrome. The therapeutic agent has favorable storage stability and can be orally or parenterally administered directly or after being mixed with a pharmaceutically acceptable carrier.

In addition, we provide a pharmaceutical composition comprising the crystal of compound (I) or of the pharmacologically acceptable salt thereof and a pharmaceutically acceptable carrier.

Further, we provide a crystal of compound (I) or of the pharmacologically acceptable salt thereof for use as a medicine.

Still further, we provide a crystal of compound (I) or of the pharmacologically acceptable salt thereof for use in the treatment of pain and, in particular, neuropathic pain or fibromyalgia syndrome.

Yet further, we provide use of the crystal of compound (I) or of the pharmacologically acceptable salt thereof for the treatment of pain and, in particular, neuropathic pain or fibromyalgia syndrome.

Yet further, we provide use of the crystal of compound (I) or of the pharmacologically acceptable salt thereof in the manufacture of a medicine for the treatment of pain and, in particular, neuropathic pain or fibromyalgia syndrome.

Yet further, we provide a method of treating pain and, in particular, neuropathic pain or fibromyalgia syndrome, comprising administering a therapeutically effective amount of the crystal of compound (I) or of the pharmacologically acceptable salt thereof to a patient in need of the treatment.

Our crystals have a strong analgesic action on pain and, in particular, neuropathic pain and/or fibromyalgia syndrome, have lower hygroscopicity than an amorphous matter thereof, and have excellent solubility and chemical and physical stability and, thus, can be favorably used as an active ingredient of a pharmaceutical product.

DETAILED DESCRIPTION

Our crystals are characterized in that they are crystals of compound (I) or the pharmacologically acceptable salt thereof. A representative example of the crystal of compound (I) is Form A crystal described in detail below. A representative example of the crystal of the salt of compound (I) is Form B crystal of ethane disulfonate.

A crystal form is identified based on characteristic peaks shown in a powder X-ray diffraction pattern and/or endothermic peaks of a differential thermal analysis curve (hereinafter referred to as "DTA curve") obtained by simultaneous thermogravimetric—differential thermal analysis (hereinafter referred to as "TG-DTA"). A powder X-ray diffraction pattern and a DTA curve may differ to some extent depending on measurement conditions. For example, it is usually acceptable that a diffraction angle 2θ on a powder X-ray diffraction pattern has a margin of error of ±0.2°.

Figure 1:
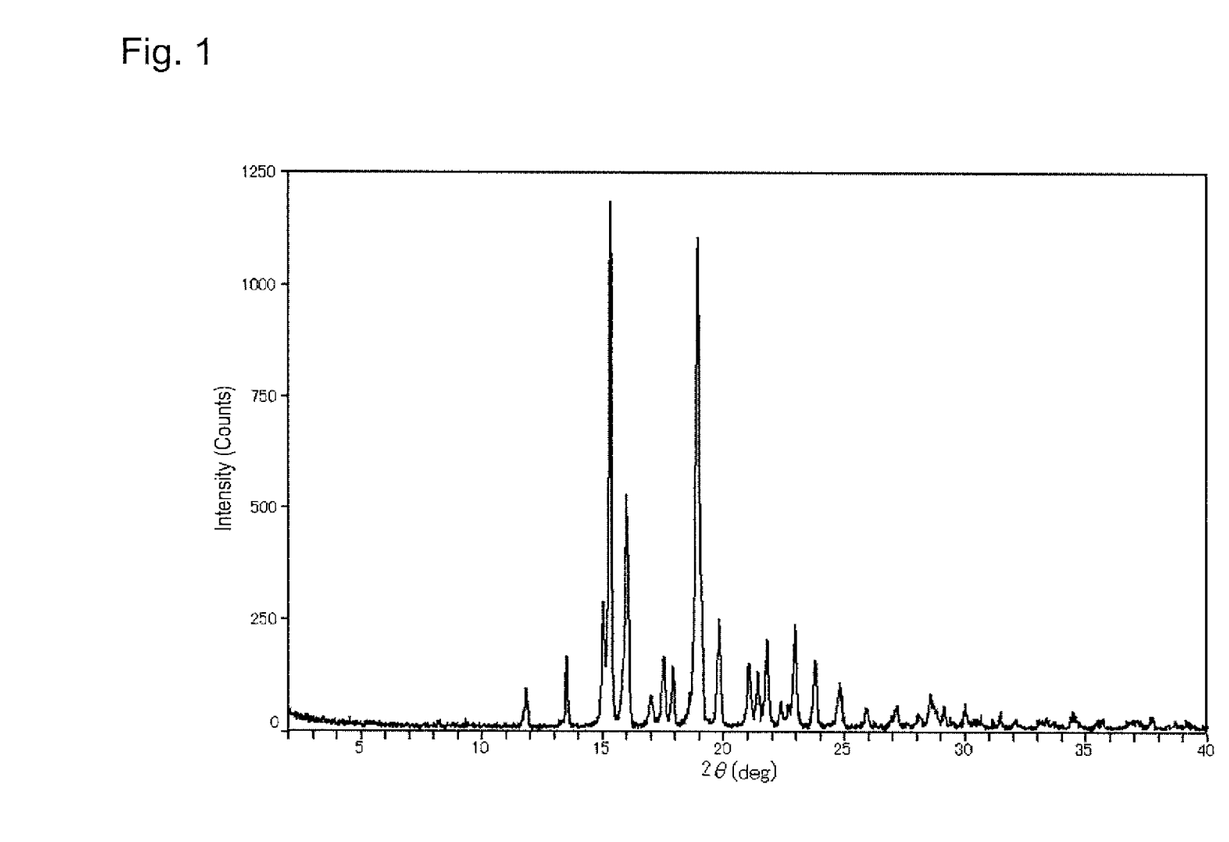
FIG. 1 is a powder X-ray diffraction pattern of Form A crystal of compound (I).

As shown in FIG. 1, Form A crystal of compound (I) is characterized in that it has peaks at diffraction angles 2θ)(° of 15.3, 16.0, 19.0, 21.8 and 23.0 in powder X-ray diffraction. In addition, Form A crystal of compound (I) gives the DTA curve shown in FIG. 2 and has an endothermic peak at 122° C., i.e., 120° C. to 124° C.

Figure 3:
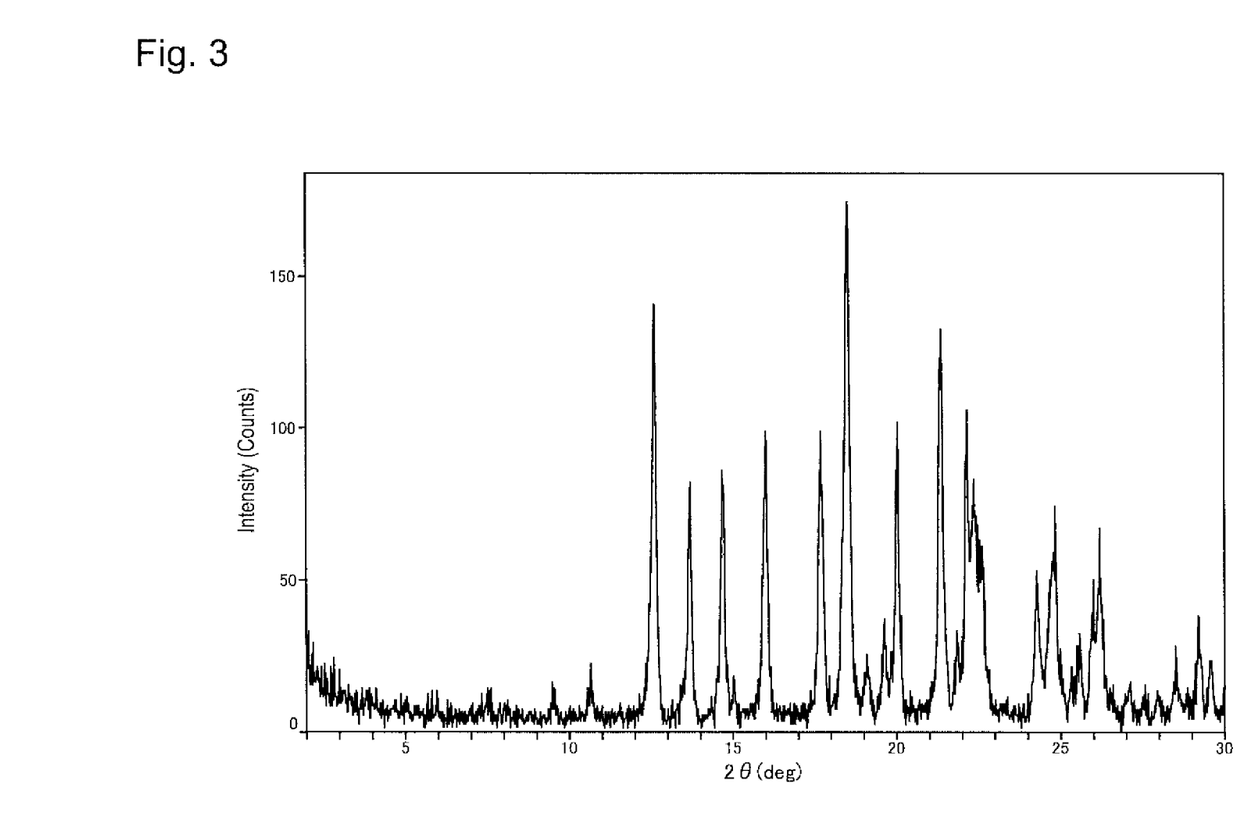
FIG. 3 is a powder X-ray diffraction pattern of Form B crystal of ethane disulfonate of compound (I).

As shown in FIG. 3, Form B crystal of ethane disulfonate of compound (I) is characterized in that it has peaks at diffraction angles 2θ)(° of 12.6, 16.0, 17.7, 18.5, and 21.3 in powder X-ray diffraction. In addition, Form B crystal of ethane disulfonate of compound (I) gives the DTA curve shown in FIG. 4 and has an endothermic peak at 175° C., i.e., 173° C. to 177° C.

Powder X-ray diffraction for obtaining a powder X-ray diffraction pattern of Form A crystal of compound (I) can be performed using a powder X-ray diffractometer under the following conditions. A measurement sample is prepared by filling a sample in a sample plate (material: silicon; depth: 0.2 mm) and leveling out the sample surface.

Powder X-Ray Diffraction Conditions
  X-ray source: CuKα radiation
  * A curved crystal monochromator (graphite) was used
  Output: 40 kV/50 mA
  Divergence slit: ½°
  Vertical slit: 5 mm
  Scattering slit: ½°
  Receiving slit: 0.15 mm
  Detector: Scintillation counter
  Scan mode: 2θ/θ scan, continuous scan
  Measurement range (2θ): 2° to 40°
  Scanning rate (2θ): 2°/min
  Scanning step (2θ): 0.02°

Powder X-ray diffraction for obtaining a powder X-ray diffraction pattern of Form B crystal of ethane disulfonate of compound (I) can be performed using a powder X-ray diffractometer under the following conditions. A measurement sample is prepared by filling a sample in a sample plate (material: silicon; depth: 0.2 mm) and leveling out the sample surface.

Powder X-Ray Diffraction Conditions
  X-ray source: CuKα radiation
  A curved crystal monochromator (graphite) was used
  Output: 40 kV/50 mA
  Divergence slit: ½°
  Vertical limiting slit: 5 mm
  Scattering slit: ½°
  Receiving slit: 0.15 mm
  Detector: Scintillation counter
  Scan mode: 2θ/θ scan, continuous scan
  Measurement range (2θ): 2° to 30°
  Scanning rate (2θ): 4°/min
  Scanning step (2θ): 0.02°

An endothermic peak refers to a temperature of the peak top on a DTA curve. TG-DTA to obtain a DTA curve can be measured using a TG-DTA system under the following conditions.

TG-DTA Conditions
  Heating rate: 5° C./min
  Atmosphere: Dry nitrogen (flow rate: 100 mL/min)
  Sample cell: Aluminum open cell
  Sample weight: 1 to 15 mg Form A crystal of compound (I) can be obtained by dissolving compound (I) in an any form in ethyl acetate at a concentration of 10 to 400 mg/mL, followed by still standing or stirring at room temperature.

Form A crystal of compound (I) can be prepared by dissolving compound (I) in an any form in a solvent, which is preferably an alcohol, aromatic, ether, ketone, ester, halogen, or nitrile solvent and adding Form A crystal of compound (I) obtained in advance as a seed crystal, followed by still standing or stirring at room temperature.

Examples of the alcohol solvent include methanol, ethanol, 1-propanol, 2-propanol, 1-butanol, 2-butanol, 2-methyl-1-propanol, 1-pentanol, and 3-methyl-1-butanol.

Examples of the aromatic solvent include benzene, chlorobenzene, toluene, xylene, and cumene.

Examples of the ether solvent include diethyl ether, tetrahydrofuran, t-butyl methyl ether, and 1,4-dioxane.

Examples of the ketone solvent include acetone, 2-butanone, 4-methyl-2-pentanone, and 2-hexanone.

Examples of the ester solvent include ethyl formate, methyl acetate, ethyl acetate, propyl acetate, isopropyl acetate, isobutyl acetate, and n-butyl acetate.

Examples of the halogen solvent include chloroform, dichloromethane, and 1,2-dichloroethene.

Examples of the nitrile solvent include acetonitrile and propionitrile.

Examples of the pharmacologically acceptable salt of compound (I) include: inorganic acid salts such as hydrochloride, sulfate, nitrate, hydrobromide, and phosphate; organic carboxylic acid salts such as acetate, trifluoroacetate, lactate, citrate, maleate, benzoate, oxalate, malonate, gluconate, glutarate, malate, tartrate, salicylate, xinafoate, ascorbate, adipate, cinnamate, fumarate, mandelate, succinate, and pamoate; and organic sulfonic acid salts such as methanesulfonate, p-toluenesulfonate, camphorsulfonate, and ethane disulfonate.

Form B crystal of ethane disulfonate of compound (I) can be obtained by adding 1,2-ethanedisulfonic acid dihydrate and distilled water to compound (I) in an any form to dissolve compound (I), removing the solvent by lyophilization, and adding acetone, followed by still standing or stirring at room temperature.

The crystal of compound (I) or the pharmacologically acceptable salt thereof can be evaluated in terms of the analgesic action and, in particular, the neuropathic pain and/or fibromyalgia syndrome treatment effect using appropriate model animals. Examples of an appropriate model animal for neuropathic pain include spinal nerve ligation model mice or rats (Kim et al., Pain, 1992, vol. 50, pp. 355-363) or partial sciatic nerve ligation model mice or rats (Malmberg et al., Pain, 1998, vol. 76, pp. 215-222). Examples of an appropriate model animal for fibromyalgia syndrome include fibromyalgia model mice or rats (Sluka et al., Journal of Pharmacology and Experimental Therapeutics, 2002, vol. 302, pp. 1146-1150; Nagakura et al., Pain, 2009, vol. 146, pp. 26-33; Sluka et al., Pain, 2009, vol. 146, pp. 3-4).

The crystal of compound (I) or the pharmacologically acceptable salt thereof has an excellent analgesic action and, in particular, an excellent neuropathic pain and/or fibromyalgia syndrome treatment effect and thus can be used as a medicine. It is used preferably as an analgesic agent and particularly preferably as a therapeutic agent for neuropathic pain and/or a therapeutic agent for fibromyalgia syndrome.

Examples of the neuropathic pain include cancer pain, shingles pain, postherpetic neuralgia, AIDS-related neuralgia, painful diabetic neuropathy, and trigeminal neuralgia.

The above-mentioned fibromyalgia syndrome refers to symptoms diagnosed as fibromyalgia syndrome by a specialist physician. Diagnosis by a specialist physician is generally done with reference to the classification standard of the American College of Rheumatology.

The crystal of compound (I) or the pharmacologically acceptable salt thereof is useful for treatment of acute and chronic pain. Acute pain is usually observed in a short period of time. Examples of acute pain include postoperative pain, pain after tooth extraction, and trigeminal neuralgia. Chronic pain is defined as a pain that lasts usually for 3 to 6 months and includes somatogenic pain and psychogenic pain. Examples of chronic pain include rheumatoid arthritis, osteoarthritis, and postherpetic neuralgia.

When the crystal of compound (I) or the pharmacologically acceptable salt thereof is administered to, for example, a mammal (e.g., a mouse, rat, hamster, rabbit, dog, monkey, bovine, sheep, or human), it exerts an excellent analgesic action and, in particular, an excellent neuropathic pain and/or fibromyalgia syndrome treatment effect.

When the crystal of compound (I) or the pharmacologically acceptable salt thereof is used as a medicine, it is possible to orally or parenterally administer the crystal of compound (I) or the pharmacologically acceptable salt thereof directly or after being mixed with a pharmaceutically acceptable carrier.

Examples of the dosage form of a medicine comprising the crystal of compound (I) or the pharmacologically acceptable salt thereof as an active ingredient for oral administration include tablets (including sugar-coated tablets and film-coated tablets), pills, granules, powders, capsules (including soft capsules and microcapsules), syrups, emulsions, and suspensions. Examples of the dosage form of a medicine comprising the crystal of compound (I) or the pharmacologically acceptable salt thereof as an active ingredient for parenteral administration include injections, infusions, drops, suppositories, endermic liniments, and adhesive patches. Further, it is also effective to combine the medicine with a suitable base (e.g., a butyric acid polymer, a glycolic acid polymer, a butyric acid-glycolic acid copolymer, a mixture of a butyric acid polymer and a glycolic acid polymer, or a polyglycerol fatty acid ester) to form a sustained-release formulation.

Formulations in the above-mentioned dosage forms can be prepared according to known preparation methods commonly used in the field of formulations. Preparations can be carried out by adding, for example, an excipient, a binder, a lubricant, a disintegrating agent, a sweetening agent, a surfactant, a suspending agent, or an emulsifying agent commonly used in the field of formulations if necessary.

Preparations of tablets can be carried out by adding, for example, an excipient, a binder, a disintegrating agent, or a lubricant, and preparations of pills and granules can be carried out by adding, for example, an excipient, a binder, or a disintegrating agent. In addition, preparations of powders and capsules can be carried out by adding, for example, an excipient, preparations of syrups can be carried out by adding, for example, a sweetening agent, preparations of emulsions or suspensions can be carried out by adding, for example, a surfactant, a suspending agent, or an emulsifying agent.

Examples of excipients include lactose, glucose, starch, sucrose, microcrystalline cellulose, powdered glycyrrhiza, mannitol, sodium hydrogen carbonate, calcium phosphate, and calcium sulfate.

Examples of binders include starch paste, a gum arabic solution, a gelatin solution, a tragacanth solution, a carboxymethylcellulose solution, a sodium alginate solution, and glycerin.

Examples of disintegrating agents include starch and calcium carbonate.

Examples of lubricants include magnesium stearate, stearic acid, calcium stearate, and purified talc.

Examples of sweetening agents include glucose, fructose, invert sugar, sorbitol, xylitol, glycerin, and simple syrup.

Examples of surfactants include sodium lauryl sulfate, polysorbate 80, sorbitan monofatty acid ester, and stearic acid polyoxyl 40.

Examples of suspending agents include gum arabic, sodium alginate, sodium carboxymethyl cellulose, methyl cellulose, and bentonite.

Examples of emulsifying agents include gum arabic, tragacanth, gelatin, and polysorbate 80.

Further, when a medicine comprising the crystal of compound (I) or the pharmacologically acceptable salt thereof as an active ingredient is prepared in any of the above dosage forms, it is possible to add a coloring agent, a preserving agent, a fragrance, a flavoring agent, a stabilizer, a thickener or the like, which is commonly used in the field of formulations.

The dose of the crystal of compound (I) or the pharmacologically acceptable salt thereof to be administered as a medicine in clinical practice can be appropriately determined depending on the symptoms, age, body weight, gender, administration method, and other factors. For example, in oral administration to an adult (body weight: about 60 kg), it is preferable to administer the medicine in one to three divided doses corresponding to an active ingredient amount of 1 to 1000 mg. In parenteral administration to an adult (body weight: about 60 kg), it is preferable to intravenously administer the medicine in the form of an injection corresponding to an active ingredient amount of 0.01 to 100 mg per body weight.

To supplement or enhance the therapeutic or prophylactic effect or to reduce the dosage, the crystal of compound (I) or the pharmacologically acceptable salt thereof may be mixed or used in combination with other drugs in an appropriate blending ratio. Examples of other drugs include: antidepressants such as amitriptyline, milnacipran, and duloxetine; anxiolytics such as alprazolam; anticonvulsants such as carbamazepine; local anesthetics such as lidocaine; sympathetic agonists such as adrenaline; NMDA receptor antagonists such as ketamine; GABA transaminase inhibitors such as sodium valproate; calcium channel blockers such as pregabalin; serotonin receptor antagonists such as risperidone; GABA receptor function enhancers such as diazepam; and anti-inflammatory drugs such as diclofenac.

Examples

Hereinafter, our derivatives and methods will be specifically described with reference to the following examples below. However, this disclosure is not limited thereto.

Compound (I) and materials and intermediates of compound (I) were synthesized by the method described in the following Reference Example. Commercially available compounds were used as compounds used for the synthesis of the reference example compounds, for which the synthesis method is not described herein.

In the following description, names of solvents shown in the NMR data indicate ones used for measurement. In addition, the 400 MHz NMR spectra were measured using a JNM-AL 400 series nuclear magnetic resonance spectrometer (manufactured by JEOL Ltd.). Chemical shifts are expressed in terms of δ (unit: ppm) based on tetramethylsilane as the reference, and signals are represented by s (singlet), d (doublet), t (triplet), q (quartet), quint (quintet), sept (septet), m (multiplet), br (broad), dd (double doublet), dt (double triplet), ddd (double doublet), dq (double quartet), td (triple doublet), and tt (triple triplet). The ESI-MS spectra were measured using Agilent Technologies 1200 Series, G6130A (manufactured by Agilent Technologies, Inc.). All solvents used herein were commercially available products. For flash column chromatography, YFLC W-prep 2XY (manufactured by Yamazen Corporation) was used.

Reference Example 1 Preparation of Amorphous Matter of Compound (I)

Chloro[(S, S)—N-[2-[2-(4-methylbenzyloxy)ethyl]amino-1,2-diphenylethyl]-p-toluenesulfonamide]ruthenium (II) catalyst (175 mg, 0.263 mmol) was added to an isopropyl alcohol (90 mL) solution of 1-(4-(dimethylamino)piperidin-1-yl)-3-(1-methyl-1H-imidazol-2-yl)propane-1,3-dione (3.0 g, 10.8 mmol) in a nitrogen gas atmosphere, and the solution was stirred at an inside temperature of 80° C. for 18 hours. The reaction solution was concentrated, and the resulting liquid was transferred to a separatory funnel with 42.8 g of distilled water. After extraction with ethyl acetate, the ethyl acetate layer was extracted with distilled water, and all aqueous layers were combined and concentrated. After concentration, ethyl acetate was added and azeotropic dehydration was carried out with an evaporator. The residue was replaced with chloroform, and the concentrate was purified by silica gel column chromatography (NH silica gel, chloroform). Drying was performed under reduced pressure at 40° C. or less for 40 hours. Thus, an amorphous matter of compound (I) (2.45 g, 8.7 mmol, 81%) was obtained. Measurement by powder X-ray diffraction was carried out, and an amorphous halo was confirmed from the results.

High performance liquid chromatography (hereinafter referred to as "HPLC"); Retention time: 19.0 min; Apparatus: Prominence HPLC system manufactured by Shimadzu Corporation; Detection wavelength: 210 nm; Column: Scherzo SS—C18, (inner diameter: 3.0 mm, length: 150 mm, particle size: 3 μm)(Imtakt Corporation); Column temperature: 40° C.; Mobile phase A: 10 mmol/L potassium dihydrogen phosphate aqueous solution/acetonitrile=90/10 (v/v); Mobile phase B: 100 mmol/L potassium dihydrogen phosphate aqueous solution/acetonitrile=50/50 (v/v); Composition of mobile phase B: 0 to 5 min: 30%, 5 to 15 min: 30→100%, 15 to 25 min: 100%, 25 to 25.1 min: 100→30%, 25.1 to 30 min: 30%; Flow rate: 1.0 mL/min; Sample injection volume: 10 μL $^1$H-NMR (400 MHz, CDCl$_3$) δ: 1.32-1.53 (2H, m), 1.82-1.92 (2H, m), 2.27-2.41 (7H, m), 2.60-2.72 (1H, m), 2.98-3.23 (3H, m), 3.77 (3H, s), 3.99-4.08 (1H, m), 4.58-4.82 (2H, m), 5.18-5.26 (1H, m), 6.86 (1H, s), 6.93 (1H, s).

ESI-MS: m/z=281 (M+H)+.

Reference Example 2 Synthesis of 1-(4-(dimethylamino)piperidin-1-yl)-3-(1-methyl-1H-imidazol-2-yl)propan-1,3-dione A tetrahydrofuran solution of lithium diisopropylamide (2.0 M, 7.05 mL, 14.1 mmol) was added dropwise to a tetrahydrofuran (20 mL) solution of 1-(4-dimethylaminopiperidin-1-yl)ethanone (1.00 g, 5.87 mmol) at −78° C. and stirred at the same temperature for 1 hour. A tetrahydrofuran solution (9.0 mL) of ethyl 1-methyl-1H-imidazole-2-carboxylate (1.09 g, 7.05 mmol) was added to the reaction solution at the same temperature, stirred for 1 hour, and further stirred at 0° C. for 1 hour. To the reaction solution, a saturated ammonium chloride aqueous solution and a potassium carbonate aqueous solution were added in that order, followed by extraction with chloroform. The organic layer was washed with a 10% sodium chloride aqueous solution, dried over anhydrous sodium sulfate, and filtered. Then, the filtrate was concentrated under reduced pressure. The residue was purified by flash column chromatography (NH silica gel, hexane/ethyl acetate), thereby obtaining 1-(4-(dimethylamino)piperidin-1-yl)-3-(1-methyl-1H-imidazol-2-yl)propan-1,3-dione (0.990 g, 3.56 mmol, 61%) as a colorless oil.

$^1$H-NMR (400 MHz, CDCl$_3$) δ: 1.32-1.5 (2H, m), 1.80-1.94 (2H, m), 2.22-41 (7H, m), 2.60-2.70 (1H, m), 3.03-3.13 (1H, m), 3.80-3.89 (1H, m), 4.01 (3H, s), 4.23 (2H, dd, J=15.6, 36.8 Hz), 4.55-4.67 (1H, m), 7.05 (1H, s), 7.14 (1H, s).

ESI-MS: m/z=279 (M+H)+.

Reference Example 3 Synthesis of 1-(4-dimethylaminopiperidin-1-yl)ethanone

Pyridine (0.922 mL, 9.75 mmol) and acetic anhydride (0.946 mL, 11.7 mmol) were added at 0° C. to a dichloromethane(7.8 mL) solution of 4-dimethylaminopiperidine (1.00 g, 7.79 mmol), and the reaction solution was stirred at room temperature for 16 hours. A saturated sodium hydrogen carbonate aqueous solution was added to the reaction solution, followed by extraction with chloroform. The organic layer was washed with a 10% sodium chloride aqueous solution, dried over anhydrous sodium sulfate, and filtered. Then, the filtrate was concentrated under reduced pressure. The residue was purified by flash column chromatography (NH silica gel, chloroform/methanol), thereby obtaining 1-(4-dimethylaminopiperidin-1-yl)ethanone (0.869 g, 6.78 mmol, 87%) as a colorless oil.

$^1$H-NMR (400 MHz, CDCl$_3$) δ: 1.30-1.47 (2H, m), 1.79-1.92 (2H, m), 2.10 (3H, s), 2.25-2.40 (7H, m), 2.53-2.63 (1H, m), 3.01-3.11 (1H, m), 3.81-3.90 (1H, m), 4.58-4.66 (1H, m).

ESI-MS: m/z=171 (M+H)+.

Reference Example 4 Synthesis of ethyl 1-methyl-1H-imidazole-2-carboxylate

Triethylamine (3.40 mL, 24.4 mmol) and Ethyl chloroformate(2.34 mL, 24.4 mmol) were added at 0° C. to an acetonitrile (4.0 mL) solution of 1-methyl-1H-imidazole (1.00 g, 12.2 mmol), and the reaction solution was stirred at room temperature for 16 hours. The reaction solution was filtered through celite, and the filtrate was concentrated under reduced pressure. The residue was purified by flash column chromatography (silica gel, hexane/ethyl acetate), thereby obtaining ethyl 1-methyl-1H-imidazole-2-carboxylate (1.50 g, 9.73 mmol, 80%) as a white solid.

$^1$H-NMR (400 MHz, CDCl$_3$) δ: 1.42 (3H, t, J=7.2 Hz), 4.01 (3H, s), 4.40 (2H, q, J=7.2 Hz), 7.01-7.03 (1H, m), 7.13-7.15 (1H, m).
ESI-MS: m/z=155 (M+H)+.

Example 1 Production of Form a Crystal of Compound (I) (Method 1)

Figure 2:
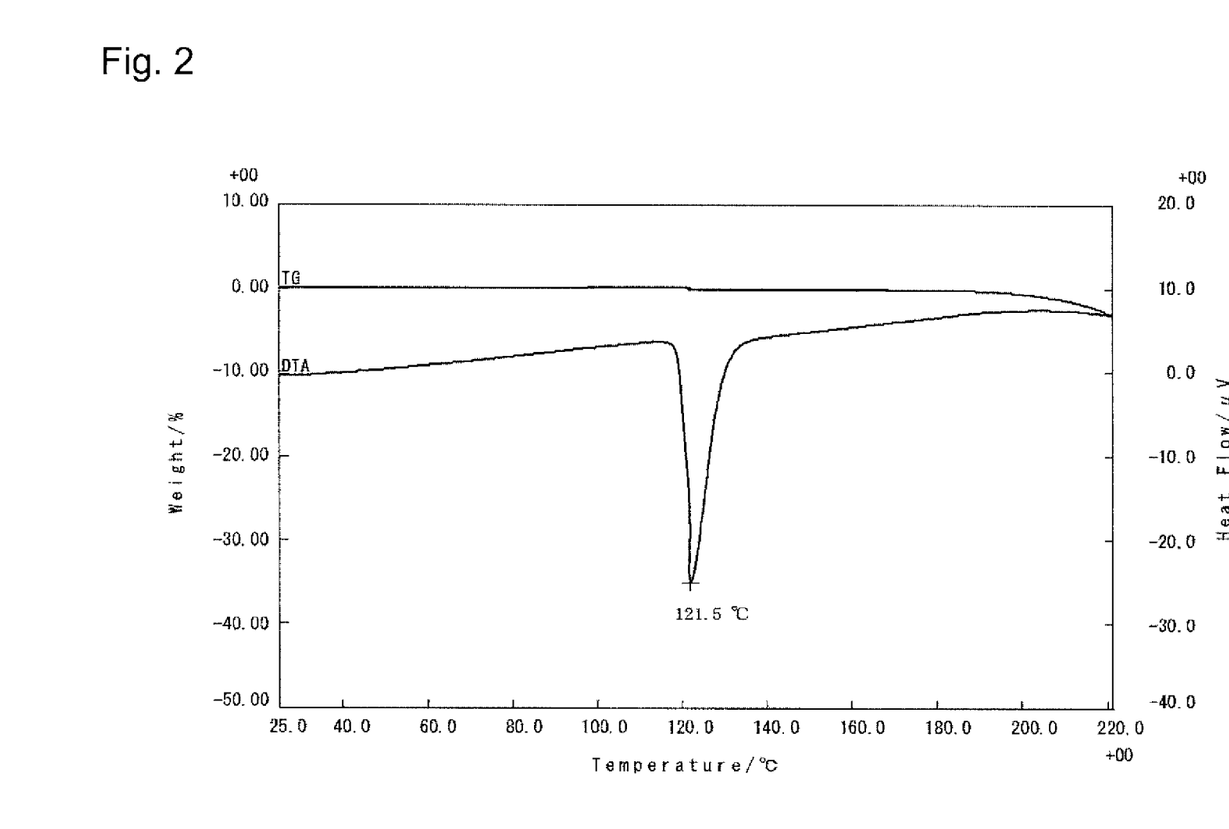
FIG. 2 is a differential thermal analysis curve obtained by simultaneous thermogravimetric—differential thermal analysis of Form A crystal of compound (I).

The amorphous matter (5 mg) of compound (I) was weighed into a borosilicate glass vial, ethyl acetate (28 μL) was added, and the matter was dissolved therein (concentration: 180 mg/mL). The vial was shaken at room temperature in an airtight state for 6 hours and then heated at 55° C. for 10 minutes. Thereafter, the vial was further shaken at room temperature for 4.5 hours. After confirming the precipitate, the solvent was removed, and vacuum drying was carried out using a vacuum pump for 30 minutes, thereby obtaining a white powder. With respect to the obtained powder, measurement of powder X-ray diffraction using a powder X-ray diffractometer (Rigaku Corporation; 2200/RINT ultima+PC) and TG-DTA using a TG-DTA system (Rigaku Corporation; TG8120) were conducted. FIGS. 1 and 2 show the measurement results.
Diffraction angle 2θ: 15.3°, 16.0°, 19.0°, 21.8°, and 23.0°
Endothermic peak: 122° C.

Example 2 Production of Form a Crystal of Compound (I) (Method 2)

The amorphous matter (5 mg) of compound (I) was weighed into a borosilicate glass vial, ethyl acetate (17 μL or 25μL) was added, and the matter was dissolved therein (concentration: 300 mg/mL or 200 mg/mL). The vial was shaken at room temperature in an airtight state for 3 days. As the precipitate was confirmed in each system, the solvent was removed, and vacuum drying was carried out using a vacuum pump for 30 minutes, thereby obtaining a white powder. With respect to the obtained solid, measurement by powder X-ray diffraction was conducted under the following conditions, and it was confirmed that the results were consistent with FIG. 1.
Powder X-Ray Diffraction Conditions
  X-ray source: CuKα radiation
  * A curved crystal monochromator (graphite) is used
  Output: 40 kV/50 mA
  Divergence slit: ½°
  Vertical limiting slit: 5 mm
  Scattering slit: ½°
  Receiving slit: 0.15 mm
  Detector: Scintillation counter
  Scan mode: 2θ/θ scan, continuous scan
  Measurement range (2θ): 2° to 30°
  Scanning rate (2θ): 20°/min
  Scanning step (2θ): 0.04°

Example 3 Production of Form a Crystal of Compound (I) (Method 3)

The amorphous matter (5 mg) of compound (I) was weighed into a borosilicate glass vial, each solvent in Table 1 was added at the corresponding addition amount in Table 1 and dissolved therein. Form A crystal (0.1 mg) of compound (1) was added as a seed crystal to the vial and, then, the mixture was shaken at room temperature for 14 hours. As the precipitate was confirmed in each system, the solvent was removed, and vacuum drying was carried out using a vacuum pump for 30 minutes, thereby obtaining a white solid. With respect to each obtained solid, measurement by powder X-ray diffraction was conducted under the following conditions, and it was confirmed that the results were consistent with FIG. 1.

TABLE 1

| Solvent type | Amount of solvent added (μL) | Crystallization examination concentration (mg/mL) | Appearance of solution | Presence or absence of precipitate |
|---|---|---|---|---|
| Acetone | 2.5 | 2000 | Soluble | White solid precipitate |
|  | 5.0 | 1000 | | |
|  | 10 | 500 | | |
|  | 28 | 180 | | |
| Tetrahydrofuran | 2.5 | 2000 | Soluble | White solid precipitate |
|  | 5.0 | 1000 | | |
|  | 10 | 500 | | |
|  | 28 | 180 | | |
| Toluene | 2.5 | 2000 | Soluble | White solid precipitate |
|  | 5.0 | 1000 | | |
|  | 10 | 500 | | |
|  | 28 | 180 | | |
| Acetonitrile | 2.5 | 2000 | Soluble | White solid precipitate |
|  | 5.0 | 1000 | | |

Powder X-ray diffraction conditions
  X-ray source: CuKα radiation
  * A curved crystal monochromator (graphite) is used
  Output: 40 kV/50 mA
  Divergence slit: 1/2°
  Vertical limiting slit: 5 mm
  Scattering slit: 1/2°
  Receiving slit: 0.15 mm
  Detector: Scintillation counter
  Scan mode: 2θ/θ scan, continuous scan
  Measurement range (2θ): 2° to 30°
  Scanning rate (2θ): 20°/min
  Scanning step (2θ): 004°

Example 4 Effects of Recrystallization on Purification of Form a Crystal of Compound (I)

Form A crystal of compound (I) (80 mg) was weighed into a borosilicate glass vial, ethyl acetate (0.8 mL) was added, and the crystal was dissolved therein with heating to 60° C. (concentration: 100 mg/mL). The vial was left to be cooled down to room temperature and stirred in an airtight state for 3 hours. The precipitate was collected by filtration, washed with ethyl acetate, and dried under reduced pressure for 1 hour using a vacuum pump, thereby obtaining a white powder. The obtained powder was subjected to measurement by powder X-ray diffraction using a powder X-ray diffractometer (Rigaku Corporation; 2200/RINT ultima+PC), and it was confirmed that the results were consistent with FIG. 1. Chemical purity and optical purity before and after recrystallization were measured by HPLC under the following conditions. Table 2 show the results. A 20 mmol/L potassium dihydrogen phosphate. 5 mmol/L sodium octane sulfonate aqueous solution (hereinafter referred to as "Solution X") to be used for preparation of an HPLC mobile phase was prepared by weighing potassium dihydrogen phosphate (8.2 g) and sodium 1-octane sulfonate (3.2 g), adding them to distilled water (3 L), and dissolving them with stirring. In addition, a sample for HPLC analysis was prepared by dissolving Form A crystal of compound (I) (1 mg) in 1 mL of methanol.

HPLC Conditions for Chemical Purity Measurement
  Apparatus: LC-30AD system manufactured by Shimadzu Corporation
  Detection wavelength: 210 nm, 300 nm
  Column: Kinetex 1.7 μm C18 (inner diameter: 2.1 mm, length: 100 mm, particle size: 1.7 μm) (Phenomenex Inc.)
  Column temperature: 40° C.
  Mobile phase A: Solution X
  Mobile phase B: Acetonitrile
  Composition of mobile phase B: 0 to 5 min: 5→50%, 5 to 7 min: 50%, 7 to 7.1 min: 50→5%, 7.1 to 10 min: 5%
  Flow rate: 0.4 mL/min
  Sample injection volume: 2.5 μL HPLC Conditions for Optical Purity Measurement
  Apparatus: LC-20AD system manufactured by Shimadzu Corporation
  Detection wavelength: 220 nm
  Column: CHIRALCEL OZ-3(inner diameter: 4.6 mm, length: 250 mm, particle size: 3 μm) (Daicel Corporation)
  Column temperature: 40° C.
  Mobile phase: Methanol/ethylenediamine (100:0.1)
  Flow rate: 0.5 mL/min
  Sample injection volume: 2 μL

TABLE 2

|  | Chemical purity | Optical purity |
|---|---|---|
| Before recrystallization | 98.4% | 89.1% ee |
| After recrystallization | 99.8% | 98.4% ee |

As shown in Table 2, Form A crystal of compound (I) was improved in terms of chemical purity and optical purity by recrystallization. These results revealed that recrystallization of the crystal of compound (I) was effective for purification.

Example 5 Production of Form B Crystal of Ethane Disulfonate of Compound (I)

Figure 4:
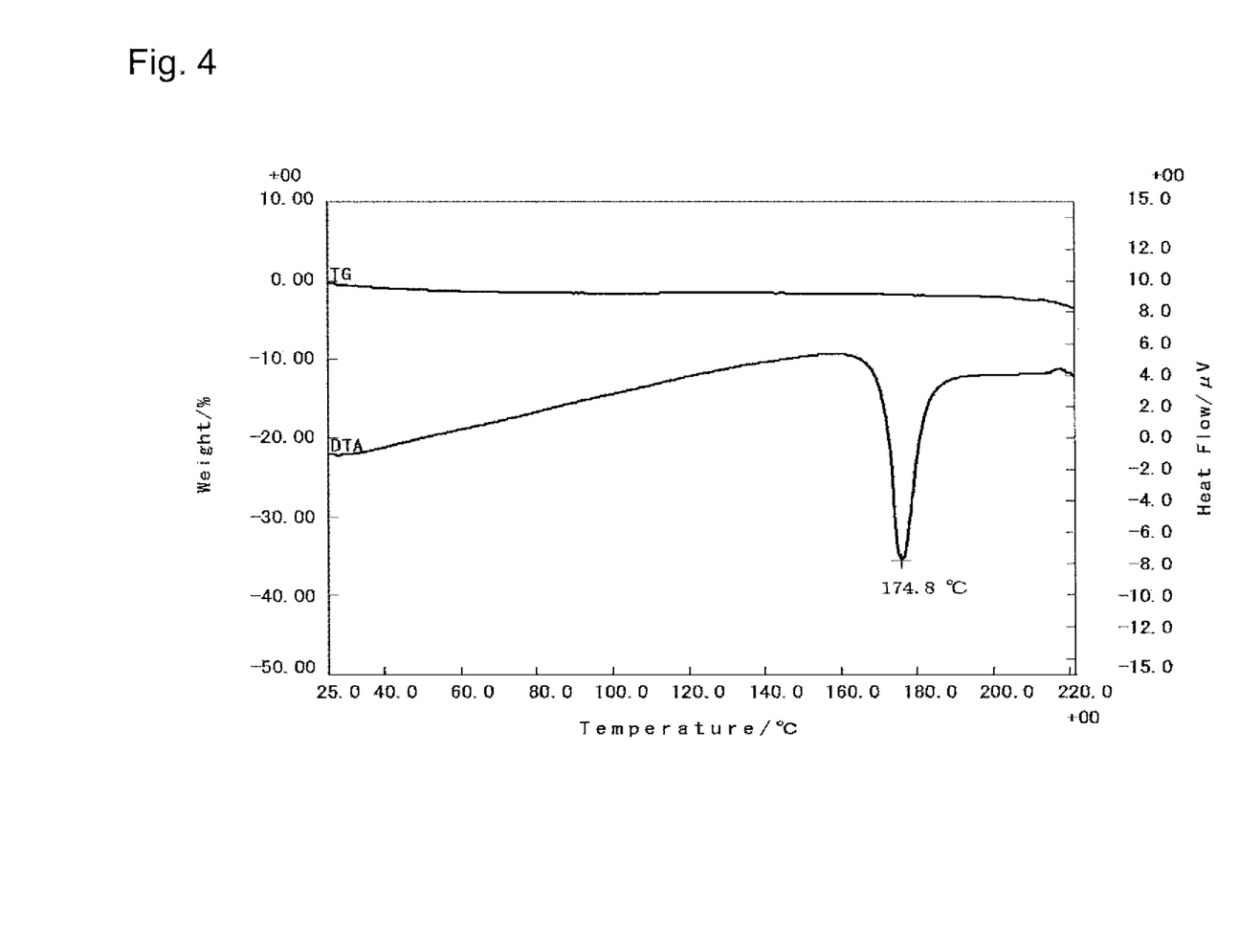
FIG. 4 is a differential thermal analysis curve obtained by simultaneous thermogravimetric—differential thermal analysis of Form B crystal of ethane disulfonate of compound (I).

1,2-Ethanedisulfonic acid dihydrate (11 mg) and distilled water (2 mL) were added to compound (I) (200 mg) to dissolve compound (I). Thereafter, the resulting solution (0.25 mL) was weighed into a borosilicate glass vial, and the solvent was removed by lyophilization. Acetone (0.13 mL) was added, and the mixture was stirred at room temperature. After confirming the precipitate, the solvent was removed by a Pasteur pipette and vacuum drying was carried out using a vacuum pump for 3 hours, thereby obtaining a white solid. With respect to the obtained solid, measurement of powder X-ray diffraction using a powder X-ray diffractometer (Rigaku Corporation; 2200/RINT ultima+PC) and TG-DTA using a TG-DTA system (Rigaku Corporation; TG8120) were conducted. FIGS. 3 and 4 show the measurement results.
  Diffraction angle 2θ: 12.6°, 16.0°, 17.7°, 18.5°, and 21.3°
  Endothermic peak: 175° C.

Example 6 Effects on Neuropathic Pain Model Rats

Analgesic effects of the crystal of compound (I) or the pharmacologically acceptable salt thereof upon neuropathic pain were evaluated using spinal nerve ligation model rats (Kim and Chung, Pain, 1992, vol. 50, p. 355). Form A crystal of compound (I) was used as a crystal of compound (I) or the pharmacologically acceptable salt thereof for evaluation.

The above model rats were prepared as follows. In experiments, 6-to 7-week-old SD male rats were used for 5 to 7 cases per group, and the lumbar skin and muscle of each rat were dissected to expose the L5 and L6 sciatic nerves under inhalation anesthesia with isoflurane. After ligating the L5 and L6 spinal nerves with silk suture, the wound of each rat was sutured. Thus, a nerve ligation group was prepared. The group in which the nerve was exposed but not ligated was determined to be a sham surgery group.

Allodynia observed in spinal nerve ligation model rats was measured using a von Frey filaments according to a method described in a known publication (Chaplan et al., J. Neurosci. Methods, 1994, vol. 53, p. 55) and a 50% response threshold (g) was determined. Eight days after the ligation surgery, allodynia of the nerve ligation group was measured before oral administration of Form A crystal of compound (I). Rats with a 50% response threshold (average value of the right hind paw and the left hind paw) of 2 g to less than 6 g were considered to have developed allodynia. The rats were divided as neuropathic pain model rats into groups such that there was no significant difference in the 50% response threshold between groups. Allodynia was measured 3 hours after the oral administration of Form A crystal of compound (I), and the analgesic effect was evaluated. Pregabalin was used as a positive control.

Form A crystal of compound (I) was dissolved in water for injection (distilled water) to result in concentrations of 5, 10, and 20 mg/mL, and orally administered in a dose volume of 1 mL per kg body weight. Pregabalin was dissolved in water for injection (distilled water) to result in a concentration of 10 mg/mL and orally administered in a dose volume of 1 mL per kg of body weight. Water for injection (distilled water) was orally administered to the sham surgery group. A group in which water for injection (distilled water) was orally administered to rats in the nerve ligation group was defined as a negative control group.

Figure 5:
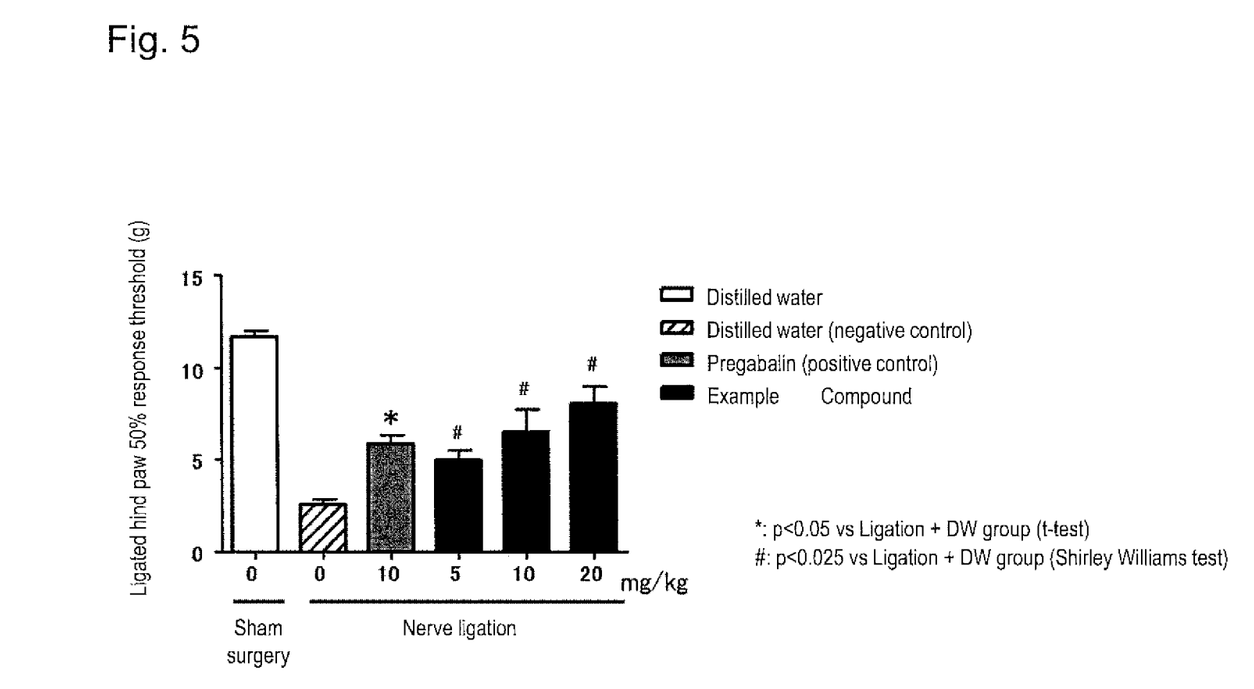
FIG. 5 is a graph showing effect of compound (I) in spinal nerve ligation model rats (oral administration).

FIG. 5 shows the results. The horizontal axis represents the solution to be administered in each group, namely, the nerve ligation group or sham surgery group, and the vertical axis represents the 50% response threshold (g) (mean±standard error, n=5 to 7). For the evaluation of efficacy, statistical processing was carried out by the independent two-group t test (group to which pregabalin was administered) or the Shirley-Williams test (group to which Form A crystal of compound (I) was administered) with respect to the negative control group as a control. Symbols "*" and "#" in FIG. 5 indicate statistical significance (*: $p<0.05$; #: $p<0.025$) for comparison with the negative control group ("nerve ligation-0 mg/kg" group in FIG. 5).

As in oral administration of 10 mg/kg of pregabalin as a positive control, oral administration of 5 mg/kg, 10 mg/kg, and 20 mg/kg of Form A crystal of compound (I) induced the significant improvement of allodynia observed in neuropathic pain model rats as compared to the negative control group. The results indicate that the crystal of compound (I) or the pharmacologically acceptable salt thereof is effective against neuropathic pain.

Example 7 Effects on Fibromyalgia Model Rats

The analgesic effect of the crystal of compound (I) or the pharmacologically acceptable salt thereof against fibromyalgia syndrome was evaluated using fibromyalgia model rats (Sluka et al., Journal of Pharmacology and Experimental Therapeutics, 2002, vol. 302, pp. 1146-1150; Nagakura et al., Pain, 2009, vol. 146, pp. 26-33; Sluka et al., Pain, 2009, vol. 146, pp. 3-4). Form A crystal of compound (I) was used as a crystal of compound (I) or the pharmacologically acceptable salt thereof for evaluation.

The above model rats were prepared as follows. In experiments, 6-to 7-week-old SD male rats were used for 5 or 6 cases per group. 100 μL of acidic physiological saline adjusted to pH 4.0 was administered twice to the gastrocnemius muscle of the right hind paw of each rat (the day of the administration of acidic physiological saline was defined as Day 1 after the start of the experiment, and single dose administrations were carried out on Days 1 and 6 after the start of the experiment) under inhalation anesthesia with isoflurane. The thus prepared group was determined to be an acidic physiological saline group. As a control for the model, a group treated with a physiological saline instead of an acidic physiological saline was determined to be a physiological saline group.

Allodynia observed in fibromyalgia model rats was measured using a von Frey filaments according to a method described in a known publication (Chaplan et al., Journal of Neuroscience Methods, 1994, vol. 53, pp. 55-63) and a 50% response threshold (g) was determined. On Day 7 after the start of the experiment, allodynia was measured 3 hours after oral administration of Form A crystal of compound (I), and the analgesic effect was evaluated. Allodynia of the acidic physiological saline group was measured before oral administration of Form A crystal of compound (I). Rats with a 50% response threshold (average value of the right hind paw and the left hind paw) of 6 g or less by intramuscular administration of acidic physiological saline were considered to have developed allodynia. The rats were divided as fibromyalgia model rats into groups such that there was no significant difference in the 50% response threshold between groups. Allodynia was measured 3 hours after the oral administration of the crystal of compound (I), and the analgesic effect was evaluated. Pregabalin was used as a positive control.

Form A crystal of compound (I) was dissolved in water for injection (distilled water) to result in concentrations of 0.1, 1, and 10 mg/mL, and orally administered in a dose volume of 1 mL per kg body weight. Pregabalin was dissolved in water for injection (distilled water) to result in a concentration of 10 mg/mL and orally administered in a dose volume of 1 mL per kg of body weight. A group in which water for injection (distilled water) was orally administered to rats in the acidic physiological saline group was defined as a negative control group.

Figure 6:
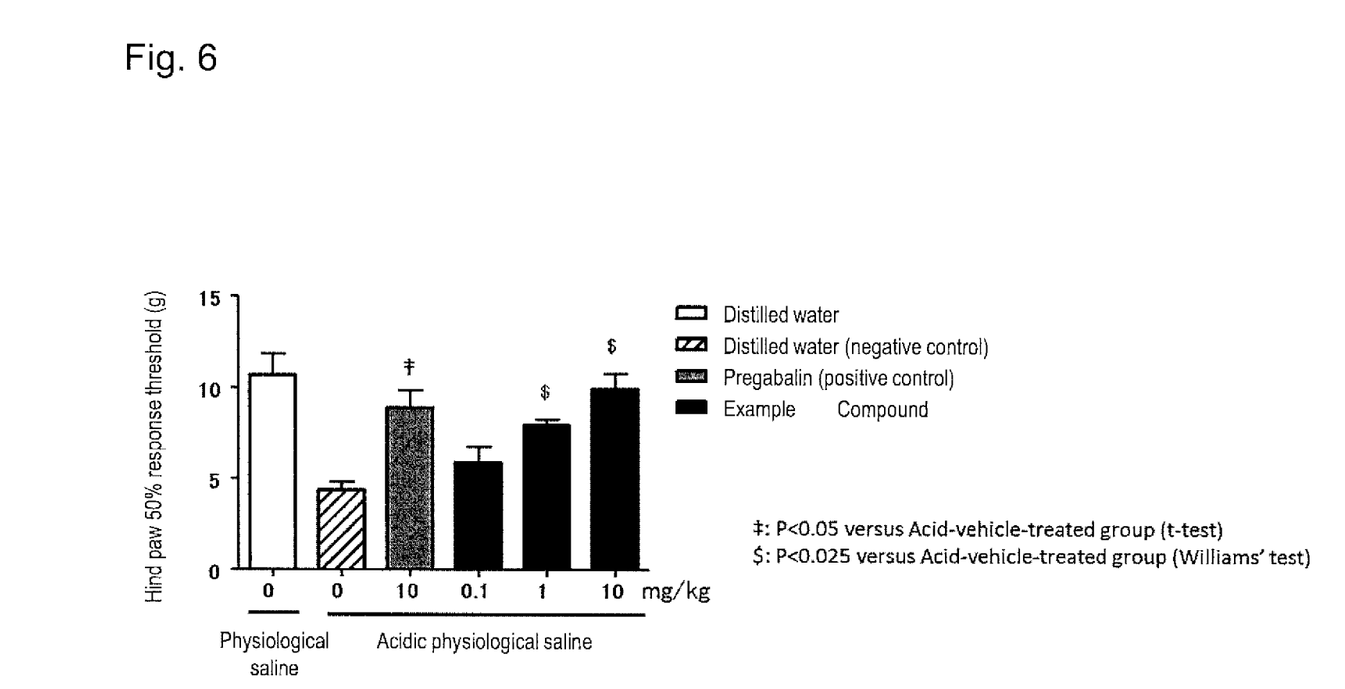
FIG. 6 is a graph showing effect of compound (I) in fibromyalgia model rats (oral administration).

FIG. 6 shows the results. The horizontal axis represents the solution to be administered in each group, namely, the acidic physiological saline group or physiological saline group, and the vertical axis represents the 50% response threshold (g) (average value of the right hind paw and the left hind paw) (mean±standard error, n=5 to 6). For the evaluation of efficacy, statistical processing was carried out by the independent two-group t test (group to which pregabalin was administered) or the Williams test (group to which the crystal of compound (I) was administered) with respect to the negative control group as a control. Symbols ‡ and $ in FIG. 6 indicate statistical significance (‡: $p<0.05$;$: $<0.025$) for comparison with the negative control group ("acidic physiological saline-0 mg/kg" group in FIG. 6).

As in oral administration of 10 mg/kg of pregabalin as a positive control, oral administration of 1 mg/kg and 10 mg/kg of Form A crystal of compound (I) induced the significant improvement of allodynia observed in fibromyalgia model rats as compared to the negative control group. The results indicate that the crystal of compound (I) or the pharmacologically acceptable salt thereof is effective against fibromyalgia syndrome.

Comparative Example 1 Examination of Acquisition of Crystals of Compound (I) (Selection of Crystallization Solvents: Examination of Initial Crystallization Using Various Solvents)

The amorphous matter (10 mg) of compound (I) was weighed into a borosilicate glass vial, each solvent in Table 3 was added at the corresponding amount of solvent added in Table 3, and confirmed whether or not the amorphous matter was dissolved. As a result, the amorphous matter was completely dissolved at 500 mg/mL or more in each solvent. Subsequently, the vial was shaken at room temperature in an airtight state for 7 days. However, no solid precipitated in either case. The amorphous matter was not dissolved at all in cyclohexane and heptane even at a low concentration (3 mg/mL). It was therefore judged that they were unsuitable as a crystallization solvent.

TABLE 3

| Solvent type | Amount of solvent added (mL) | Crystallization examination concentration (mg/mL) | Appearance of solution | Presence or absence of precipitate |
| --- | --- | --- | --- | --- |
| Methanol | 0.02 | 500 | Soluble | No precipitate |
| | 0.005 | 2000 | Soluble | No precipitate |
| Ethanol | 0.02 | 500 | Soluble | No precipitate |
| 1-Propanol | 0.02 | 500 | Soluble | No precipitate |
| 2-Propanol | 0.02 | 500 | Soluble | No precipitate |
| | 0.005 | 2000 | Soluble | No precipitate |
| 1-Butanol | 0.02 | 500 | Soluble | No precipitate |
| Chlorobenzene | 0.02 | 500 | Soluble | No precipitate |
| Toluene | 0.02 | 500 | Soluble | No precipitate |
| | 0.005 | 2000 | Soluble | No precipitate |
| Tetrahydrofuran | 0.02 | 500 | Soluble | No precipitate |
| | 0.01 | 1000 | Soluble | No precipitate |
| Acetone | 0.02 | 500 | Soluble | No precipitate |
| | 0.01 | 1000 | Soluble | No precipitate |
| 2-Butanone | 0.02 | 500 | Soluble | No precipitate |
| 4-Methyl-2-pentanone | 0.02 | 500 | Soluble | No precipitate |

TABLE 3-continued

| Solvent type | Amount of solvent added (mL) | Crystallization examination concentration (mg/mL) | Appearance of solution | Presence or absence of precipitate |
|---|---|---|---|---|
| Ethyl acetate | 0.02 | 500 | Soluble | No precipitate |
|  | 0.01 | 1000 | Soluble | No precipitate |
|  | 0.005 | 2000 | Soluble | No precipitate |
| Ethyl formate | 0.02 | 500 | Soluble | No precipitate |
| Methyl acetate | 0.02 | 500 | Soluble | No precipitate |
| Isopropyl acetate | 0.02 | 500 | Soluble | No precipitate |
| Isobutyl acetate | 0.02 | 500 | Soluble | No precipitate |
| Chloroform | 0.02 | 500 | Soluble | No precipitate |
|  | 0.005 | 2000 | Soluble | No precipitate |
| Acetonitrile | 0.02 | 500 | Soluble | No precipitate |
|  | 0.005 | 2000 | Soluble | No precipitate |
| Cyclohexane | 0.02 | 500 | Insoluble | — |
|  | 3 | 3 | Insoluble | — |
| Heptane | 0.02 | 500 | Insoluble | — |
|  | 3 | 3 | Insoluble | — |
| Water | 0.02 | 500 | Soluble | No precipitate |

These results revealed that no crystals of compound (I) can be obtained even at high solute concentrations of 500 mg/mL or more. In addition, as these solvents are extremely high in solubility at room temperature, it can be judged that they are not suitable as a crystallization solvent.

Example 8 Evaluation of Hygroscopicity

Equilibrium moisture measurement was performed on Form A crystal and the amorphous matter of compound (I) under the following conditions using a fully automated symmetric vapor sorption analyzer (TA Instruments Inc.; VTI-SA+). The weight increase amount (moisture absorptivity) as a result of humidification with an increase in relative humidity from 5% to 70% was evaluated. The change in appearance was also observed. Table 4 shows the results.
Equilibrium Moisture Measurement Conditions
  Sample amount: 5 to 15 mg
  Measurement temperature: 30° C.
  Equilibrium weight/time: 0.01 wt %/5 minutes
  Maximum time of equilibrium: 180 minutes
  Measurement range: Relative humidity of 5%-Relative humidity of 70%-Relative humidity of 5%
  Measurement step: Relative humidity of 5%

In addition, to evaluate the presence or absence of change in the crystal form, measurement of powder X-ray diffraction was carried out for Form A crystal after the hygroscopicity evaluation test.

Form A crystal of compound (I) did not experience an increase in weight upon humidification up to a relative humidity of 65%, did not deliquesce, and also did not experience a change in the crystal form. On the other hand, the amorphous matter deliquesced at a relative humidity of less than 5% and turned into oil matter. These results revealed that the crystal of compound (I) or the pharmacologically acceptable salt thereof has excellent physical stability.

TABLE 4

|  | Weight increase† | Change in appearance |
|---|---|---|
| Form A crystal | 0.1% | Maintenance of white powder (No deliquescence) |

Symbol "†" represents the weight increase amount upon humidification with an increase in relative humidity from 5% to 65%.

Example 9 Evaluation of Solubility

Form A crystal of compound (I) (100 mg) was weighed into a borosilicate glass vial, and the 1st fluid for disintegration test/1st fluid for dissolution test of the Japanese Pharmacopoeia 16th edition (pH 1.2)(1 mL) or the 2nd fluid for disintegration test of the Japanese Pharmacopoeia 16th edition (pH 6.8)(1 mL) was added in a temperature and humidity test chamber (Amefrec Co., Ltd.; NO DOORα) adjusted to 37° C., followed by stirring. Form B crystal of ethane disulfonate of compound (I) (10 mg) was weighed into a borosilicate glass vial, and the 2nd fluid for disintegration test of the Japanese Pharmacopoeia 16th edition (pH 6.8) (0.1 mL) was added in a temperature and humidity test chamber (Amefrec Co., Ltd.; NO DOORα) adjusted to 37° C., followed by stirring. After 30 minutes, the inside of each vial was visually checked, and it was confirmed that each crystal was completely dissolved.

TABLE 5

|  | Solvent type | Solubility (37° C.) |
|---|---|---|
| Form A crystal | 1st fluid for disintegration test/1st fluid for dissolution test of the Japanese Pharmacopoeia 16th edition (pH 1.2) | >100 mg/mL |
|  | 2nd fluid for disintegration test of the Japanese Pharmacopoeia 16th edition (pH 6.8) | >100 mg/mL |
| Form B crystal of ethane disulfonate | 2nd fluid for disintegration test of the Japanese Pharmacopoeia 16th edition (pH 6.8) | >100 mg/mL |

As shown in Table 5, Form A crystal of compound (I) and Form B crystal of ethane disulfonate of compound (I) had solubilities of 100 mg/mL or more. These results revealed that the crystal of compound (I) or the pharmacologically acceptable salt thereof is extremely excellent in solubility.

Example 10 Evaluation of Storage Stability

Form A crystal and amorphous matter of compound (I) were stored at 40° C. in an airtight state for 8 weeks or at 60° C. in an airtight state for 4 weeks. Chemical purity and optical purity before and after storage were measured by HPLC under the following conditions. Table 6 shows the results. In addition, a sample for HPLC analysis was prepared by dissolving Form A crystal of compound (I) (1 mg) or the amorphous matter of compound (I) (1 mg) in 1 mL of methanol.

HPLC Conditions for Chemical Purity Measurement
   Apparatus: LC-30AD system manufactured by Shimadzu Corporation
   Detection wavelength: 210 nm, 300 nm
   Column: Kinetex C18 (inner diameter: 2.1 mm, length: 100 mm, particle size: 1.7 μm) (Phenomenex Inc.)
   Column temperature: 40° C.
   Mobile phase A: Solution X
   Mobile phase B: Acetonitrile
   Composition of mobile phase B: 0 to 5 min: 5→50%, 5 to 7 min: 50%, 7 to 7.1 min: 50→5%, 7.1 to 10 min: 5%
   Flow rate: 0.4 mL/min
   Sample injection volume: 2.5 μL HPLC Conditions for Optical Purity Measurement
   Apparatus: LC-20AD system manufactured by Shimadzu Corporation
   Detection wavelength: 220 nm
   Column: CHIRALCEL OZ-3(inner diameter: 4.6 mm, length: 250 mm, particle size: 3 μm)(Daicel Corporation)
   Column temperature: 40° C.
   Mobile phase: Methanol/ethylenediamine (100:0.1)
   Flow rate: 0.5 mL/min
   Sample injection volume: 2 μL

TABLE 6

| | | Form A | | Amorphous matter | |
|---|---|---|---|---|---|
| Storage condition | Temperature | 40° C. | 60° C. | 40° C. | 60° C. |
| | Relative humidity | 75% | — | 75% | — |
| | Package type | Airtight state | Airtight state | Airtight state | Airtight state |
| | Period | 8 weeks | 4 weeks | 8 weeks | 4 weeks |
| Chemical purity(%) | Initial value | 99.9 | 99.9 | 99.9 | 99.9 |
| | After storage | 99.9 | 99.8 | 97.2 | 91.5 |
| Decomposition product increased by not less than 0.15% after storage | | None | None | 4 different products[1] | 7 different products[2] |
| Optical purity (% ee) | Initial value | 98.6 | 98.6 | 98.6 | 98.6 |
| | After storage | 98.8 | 98.8 | 98.7 | 98.9 |

[1]Increases in the amounts of respective decomposition products were as follows in relation to relative retention time (hereinafter referred to as "RRT"; RRT is calculated from retention time of HPLC chromatogram for a decomposition product/retention time of HPLC chromatogram for the compound): a decomposition product for RRT of 0.8: 0.40%; a decomposition product for RRT of 0.8: 0.60%; a decomposition product for RRT of 0.9: 1.47%; and a decomposition product for RRT of 1.1: 0.21%.
[2]Increases in the amounts of respective decomposition products were as follows: a decomposition product for RRT of 0.7: 0.16%; a decomposition product for RRT of 0.8: 0.63%; a decomposition product for RRT of 0.8: 2.22%; a decomposition product for RRT of 0.9: 3.71%; a decomposition product for RRT of 1.1: 0.17%; a decomposition product for RRT of 1.1: 0.59%; and a decomposition product for RRT of 1.2: 0.45%.

As shown in Table 6, the purity of the crystal of compound (I) or the pharmacologically acceptable salt thereof did not change compared to the initial value after storage in an airtight state under accelerated conditions, and we found that the crystal of compound (I) or the pharmacologically acceptable salt thereof is extremely excellent in chemical stability as compared to the amorphous matter.

Example 11 Evaluation of Storage Stability of Form a Crystal

Form A crystal of compound (I) was stored under three storage conditions (storage test 1: 25° C., relative humidity of 60%, in an open state for 6 months; storage test 2: 40° C., relative humidity of 75%, in an airtight state for 6 months; storage test 3: 60° C., in an airtight state for 6 months), and the chemical purity and optical purity before and after storage were measured by HPLC. HPLC conditions are described below. A 5 mmol/L potassium dihydrogen phosphate aqueous solution (hereinafter referred to as "solution Y") to be used for preparation of an HPLC mobile phase was prepared by weighing potassium dihydrogen phosphate (1.4 g), adding it to distilled water (2.1 L), and dissolving it with stirring. In addition, a 200 mmol/L potassium dihydrogen phosphate aqueous solution (hereinafter referred to as "solution Z") was prepared by weighing potassium dihydrogen phosphate (40.8 g), adding it to distilled water (1.5 L), and dissolving it with stirring. Samples for HPLC analysis were each prepared by weighing the crystal (10 mg) of compound (I) into a 10 mL volumetric flask and adding a liquid mixture of solution Y/acetonitrile=70: 30 (v/v) to adjust the total volume to 10 mL.

HPLC Conditions for Chemical Purity Measurement
   Apparatus: LC-10ADvp system manufactured by Shimadzu Corporation
   Detection wavelength: 210 nm
   Column: Scherzo SS—C18(inner diameter: 4.6 mm, length: 150 mm, particle size: 3 μm)(Imtakt Corporation)
   Column temperature: 30° C.
   Mobile phase A: Solution Y/acetonitrile=70:30(v/v)
   Mobile phase B: Solution Z/acetonitrile=50:50(v/v)
   Composition of mobile phase B: 0 to 5 min: 0%, 5 to 50 min: 0→35%, 50 to 60 min: 35→100%, 60 to 83 min: 100%, 83 to 83.1 min: 100→0%, 83.1 to 95 min: 0%
   Flow rate: 1.0 mL/min
   Sample injection volume: 10 μL HPLC Conditions for Optical Purity Measurement
   Apparatus: LC-10ADvp system manufactured by Shimadzu Corporation
   Detection wavelength: 220 nm
   Column: CHIRALCEL OZ-3(inner diameter: 4.6 mm, length: 250 mm, particle size: 3 μm)(Daicel Corporation)
   Column temperature: 30° C.
   Mobile phase: Methanol/1-propanol/ethylenediamine (60:40:0.1)
   Flow rate: 0.3 mL/min
   Sample injection volume: 20 μL In addition, powder X-ray diffraction measurement and TG-DTA were performed to evaluate the presence or absence of change in the crystal form by storage. Table 7 shows the results.

TABLE 7

| | | Storage test 1 | Storage test 2 | Storage test 3 |
|---|---|---|---|---|
| Storage condition | Temperature | 25° C. | 40° C. | 60° C. |
| | Relative humidity | 60% | 75% | — |
| | Package type | Open state | Airtight state | Airtight state |
| | Period | 6 months | 6 months | 6 months |
| Chemical purity (%) | Initial value | 99.8 | 99.8 | 99.8 |
| | After 6 months | 99.8 | 99.8 | 99.8 |
| Decomposition product increased by not less than 0.15% after 6 months | | None | None | None |
| Optical purity (% ee) | Initial value | 98.8 | 98.8 | 98.8 |
| | After 6 months | 99.0 | 99.0 | 99.0 |
| Crystal form after 6 months | | Form A | Form A | Form A |

As shown in Table 7, in any of storage tests 1 to 3, the purity of Form A crystal of compound (I) did not change, and no change was observed in the crystal form. These results revealed that the crystal of compound (I) or the pharmacologically acceptable salt thereof was extremely excellent in chemical and physical stability.

The invention claimed is:

1. A crystal of ethane disulfonate of (S)-1-(4-(dimethylamino)piperidin-1-yl)-3-hydroxy-3-(1-methyl-1H-imidazol-2-yl)propan-1-one, having peaks at diffraction angles 2θ)(°) of 12.6±0.2, 16.0±0.2, 17.7±0.2, 18.5±0.2, and 21.3±0.2 in powder X-ray diffraction.

2. The crystal according to claim 1, having an endothermic peak at 173° C. to 177° C. in simultaneous thermogravimetric-differential thermal analysis.

* * * * *

UNITED STATES PATENT AND TRADEMARK OFFICE
CERTIFICATE OF CORRECTION

PATENT NO. : 11,834,431 B2  
APPLICATION NO. : 17/172240  
DATED : December 5, 2023  
INVENTOR(S) : Kanako et al.

Page 1 of 1

It is certified that error appears in the above-identified patent and that said Letters Patent is hereby corrected as shown below:

On the Title Page

At item (57) at Line 3, please change "$2\theta$)( °" to --$2\theta$ (°)--.

In the Specification

In Column 4

At Line 46, please change "$2\theta$" to --$2\theta$--; and

At Line 57, please change "$2\theta$)( °" to --$2\theta$ (°)--.

In Column 12

At Line 38, please change "004 °" to --0.04°--.

Signed and Sealed this  
Twenty-fifth Day of February, 2025

Coke Morgan Stewart  
*Acting Director of the United States Patent and Trademark Office*